United States Patent
Boit et al.

(10) Patent No.: US 10,105,314 B2
(45) Date of Patent: Oct. 23, 2018

(54) ORODISPERSIBLE MANNITOL

(71) Applicant: ROQUETTE FRERES, Lestrem (FR)

(72) Inventors: Baptiste Boit, Lestrem (FR); Philippe Lefevre, Haverskerque (FR); Damien Passe, Douai (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 15/218,234

(22) Filed: Jul. 25, 2016

(65) Prior Publication Data

US 2016/0331681 A1 Nov. 17, 2016

Related U.S. Application Data

(62) Division of application No. 13/001,501, filed as application No. PCT/FR2009/051293 on Jul. 2, 2009, now Pat. No. 9,839,610.

(30) Foreign Application Priority Data

Jul. 4, 2008 (FR) ..................... 08 54584

(51) Int. Cl.
- A61K 9/14 (2006.01)
- A61K 9/20 (2006.01)
- A61K 9/00 (2006.01)
- A61K 9/16 (2006.01)
- A61J 3/10 (2006.01)

(52) U.S. Cl.
CPC .............. *A61K 9/0056* (2013.01); *A61J 3/10* (2013.01); *A61K 9/1623* (2013.01); *A61K 9/1652* (2013.01); *A61K 9/2018* (2013.01); *A61K 9/2059* (2013.01)

(58) Field of Classification Search
CPC ... A61K 9/0056; A61K 9/1623; A61K 9/1652
See application file for complete search history.

(56) References Cited

U.S. PATENT DOCUMENTS

| | | | |
|---|---|---|---|
| 6,544,552 | B2 | 4/2003 | Sparks et al. |
| 2002/0035248 | A1 | 3/2002 | Luhn |
| 2003/0114717 | A1 | 6/2003 | Erdmann et al. |
| 2004/0180085 | A1 | 9/2004 | Ohkouchi et al. |
| 2005/0232988 | A1 | 10/2005 | Venkatesh et al. |

FOREIGN PATENT DOCUMENTS

| | | |
|---|---|---|
| EP | 0743850 | 11/1996 |
| EP | 1022021 | 7/2000 |
| EP | 1153616 | 11/2001 |
| EP | 1175899 | 1/2002 |
| EP | 1369109 | 12/2003 |
| JP | 2000273039 | 10/2000 |
| WO | 9301805 | 2/1993 |
| WO | 9852541 | 11/1998 |
| WO | 0047233 | 8/2000 |
| WO | 02069934 | 9/2002 |
| WO | 03051338 | 6/2003 |
| WO | 03103629 | 12/2003 |
| WO | 2006085497 | 8/2006 |

OTHER PUBLICATIONS

CMC-IM Working Group, "Pharmaceutical Development Case Study: "ACE Tablets"", Conformia, Mar. 13, 2008, Version 2.0, pp. 1-92.
Database WPI Week 200660, Thomson Scientific, London, GB; An 2006-586537, XP002518117, Cited in ISR.
Database WPI Week 200111, Thompson Scientific, London, GB; An 2001-094833, XP002518118, Cited in ISR.
International Search Report, dated Nov. 23, 2009, from corresponding PCT application.

*Primary Examiner* — Kyle A Purdy
(74) *Attorney, Agent, or Firm* — Oliff PLC

(57) ABSTRACT

Coagglomerates of mannitol, whose laser volume-average diameter D4,3 is between 1 and 200 μm, and of granular starch, are characterized in that they have a disintegration behavior determined according to a test A such that the relaxation time measured is between 30 and 100 seconds and the swelling force is between 0.8 and 3.0 N.

15 Claims, No Drawings

ORODISPERSIBLE MANNITOL

The subject of the present invention is a coagglomerate of mannitol having a fine particle size and of granular starch which is orodispersible, and also the method for obtaining this coagglomerate.

The pharmaceutical industry consumes many tons of starch and mannitol. These are in particular used as excipients in dry forms represented, for example, by powders for filling hard gelatin capsules, sachet powders to be extemporaneously dispersed or dissolved in water, oral solid forms and tablets.

The past decade has seen the generalization of portable pharmaceutical formulations, medicaments which can be carried around at all times and taken anywhere.

These portable pharmaceutical formulations exist more particularly in orodispersible or fast-dissolving form and have the particularity of dissolving, melting or disintegrating in the mouth in a few seconds without water and chewing.

They are conventionally produced according to various technologies, from various compositions, and are mainly sold in the form of tablets, in freeze-dried form and, more recently, in the form of a film (termed "strip").

The various technologies include mainly:
freeze-drying,
molding (compression-hot molding-flash-heat process),
direct compression,
sublimation.

These formulations have changed a great deal over the past few years since the manufacturers of orodispersible forms are constantly seeking to improve the taste, the organoleptic sensation, the disintegration time in the mouth, the dissolution, the stability, the hardness, the friability, etc.

These modifications are, however, introduced mainly by adding multiple ingredients:
by adding sugar and polyol base ingredients (direct compression excipients, sweeteners, fillers),
by adding agents with a strong disintegrating capacity, commonly known as "superdisintegrants" and/or by adding effervescent agents,
by adding surfactants and/or salivation activators.

In the orodispersible tablet field, the most important characteristics for evaluating the excipients in powder form and the formulation resulting from the mixing of these powders are:
the flow capacity in the manufacturing equipment: regular feeding of the tableting chamber (i.e. the die) from the hopper,
the resistance to abrasion (or non-friability), and
the cohesion after compacting of the particles, which determines the hardness of the tablets.

The tablets produced must, however, be sufficiently hard to withstand breaking, but at the same time have good disintegration properties.

Among the excipients most commonly encountered in the preparation of orodispersible tablets, mention may particularly be made of:
mannitol, sorbitol, erythritol, maltitol, isomalt and palatinol,
cellulose, starch,
lactose, sucrose, glucose, fructose, maltose, trehalose and palatinose.

Microcrystalline cellulose meets all the requirements expected of a direct compression excipient, but it remains difficult to produce and relatively expensive.

It also has the drawback of causing a decrease in the hardness of the tablets following water uptake during storage. In addition, it causes a very unpleasant sensation in the mouth, a feeling of suffocation related to the fact that the mucous membranes dry out too rapidly.

Starch has good disintegrating properties owing to its swelling capacity in water, but, unlike superdisintegrants, for this to be the case, it must be incorporated in large amounts, generally greater than 15% of the final formulation.

Starch can also serve as a diluent and even, at low concentration, as a flow-promoting agent, or even as a binder when it is precooked.

On the other hand, because of the small size of its particles and its low density, it has the drawback of not flowing. The high elasticity of its granules gives it a very poor tableting capacity which is insufficient for the production of tablets of satisfactory hardness.

Lactose is a diluent which is widely used in tablet technology. It exists in two main forms: crystalline and spray-dried.

In order to improve its compression properties, lactose has been modified by spray-drying and agglomeration.

Spray-dried lactose is highly compressible and the sphericity of its particles gives it satisfactory flow properties, but it is less stable and has a shorter shelf-life than crystalline lactose.

In addition, it does not have disintegrating properties.

Tablets produced from spray-dried lactose develop a yellowish color during storage which is stronger than that developed by crystalline lactose monohydrate.

Agglomerated lactose is a stable powder which flows well, but is less compressible than spray-dried lactose.

The tableting capacity of lactose remains insufficient but it has been possible to improve it by adding to the lactose a binding or diluting excipient having a better tableting capacity, such as a microcrystalline cellulose.

However, microcrystalline celluloses have the drawbacks of being expensive and of having a very unpleasant sensation in the mouth (as already mentioned above), and that of a decrease in the hardness of the tablets formed, following water uptake.

The applicant company has, for its part, proposed, in its patent EP 1.175.899, a composition of starch and lactose granules having reduced friability, efficient flow, good tableting capacity and satisfactory disintegrating properties, while being only slightly hygroscopic.

In order to obtain such granules, the applicant company had observed that it was advisable to use a granular starch and lactose mixture and to modify its physical characteristics by using an appropriate process such that moderate friability, satisfactory tableting capacity and efficient flow are simultaneously obtained, while preserving the disintegrating properties.

In the field of polyol use as regards the field that will be specifically addressed in the present invention, namely pharmaceutical excipients and bulk sweeteners used in the food industry, no satisfactory solution has yet been really proposed.

Several pulverulent polyols are commonly used. These are sorbitol and xylitol, but especially mannitol.

This is because mannitol, owing to the low hygroscopic nature of its crystalline form, could constitute an excellent excipient, in particular for its stability with respect to active agents.

Mannitol is, among the soluble excipients, the one which confers the greatest stability on solid medicament forms, by virtue of its very high chemical inertia with respect to the active ingredients and its lack of water absorption.

Unfortunately, the product obtained by crystallization from water using a supersaturated solution still exhibits excessive friability.

In addition, the already mediocre flow properties of mannitol crystallized from water, owing to the orthorhombic structure of its crystals, become particularly poor when said mannitol contains fine particles.

This is in particular detrimental to the filling and emptying of the hoppers and channels for feeding the devices used.

Many solutions have been proposed in order to attempt to remedy these difficulties, without however giving complete satisfaction.

In the field of the production of orodispersible tablets by spray-drying or by direct compression, mention may, for example, be made of:

international patent application WO 98/52541 which describes fast-dissolving chewable tablets produced from low density granules obtained either by spray-drying or by compacting of low-density ingredients such as water-soluble carbohydrates (such as mannitol), but requiring the addition of alkaline-earth metal salts (calcium carbonate, magnesium carbonate, inter alia), patent EP 743.850, which uses the spray-drying technique to produce fast-dissolving tablets.

However, these tablets are produced by spray-drying a mixture of hydrolyzed gelatin, nonhydrolyzed gelatin, mannitol as filler (60% to 96%), and a particulate porous powder which serves as a particulate support matrix for one or more pharmaceutical active agents.

In addition to the use of gelatin, other ingredients can also be added, such as disintegrating agents;

international patent application WO 93/01805 which covers multiparticulate tablets that disintegrate in less than 60 seconds, comprising an active substance, but which must comprise at least one superdisintegrant (crosslinked carboxymethylcellulose or crosslinked polyvinylpyrrolidone) and at least one swelling agent (starch, modified starch or microcrystalline cellulose) and, optionally, a direct compression sugar.

The active substance is multiparticulate and is in the form of coated microcrystals or coated microgranules.

international patent application WO 02/69934, which describes a fast-disintegration preparation prepared from the mixture of an active agent and a pulverulent powder (mannitol, xylitol, sorbitol, erythritol), the particles of which have an average diameter of between 5 and 150 µm.

The pulverulent powder is prepared by spray-drying, but must also contain a superdisintegrant.

patent application WO 00/47233, which covers a tablet preparation comprising the physical mixture of an active ingredient, a starch, and a water-soluble excipient chosen from mannitol and lactose, to which it is nevertheless necessary to add one or more lubricants chosen from magnesium stearate, calcium stearate, sodium stearyl fumarate and light silicic anhydride;

international patent application WO 03/51338, which relates to orodispersible tablets prepared by direct compression, which disintegrate in less than 60 seconds. However, it involves a co-spray-dried or co-granulated material comprising mannitol and sorbitol with ingredients such as an active agent and a superdisintegrant;

international patent application WO 03/103629, which describes tablets that disintegrate in less than 30 seconds, comprising, in addition to the spray-dried mannitol, an active ingredient, microcrystalline cellulose as superdisintegrant, and also sodium croscarmellose (as insoluble absorbent) and a lubricant.

In the above patent applications, the result is that mannitol, which is the essential excipient for avoiding water uptake by the tablets and the resulting instability, must often be incorporated with superdisintegrants which are, on the contrary, extremely water-thirsty excipients, which thus results in the opposite of what is desired.

The objective of the invention is therefore to remedy these drawbacks and the applicant company has, to its merit, found, after numerous studies, that this objective can be achieved as long as coagglomerates based on granular starch and mannitol of fine particle size are used.

The term "granular starch" is intended to mean native starches of any natural or hybrid origins, of granular type, and all the chemically modified starches which have kept a granular form.

Use will preferably be made of a white corn starch such as the product sold by the applicant company under the name "extra-white starch" which makes it possible to obtain granules with an entirely satisfactory whiteness.

The term "mannitol of fine particle size" is intended to mean a mannitol crystallized from water, the laser mean volume diameter D4,3 of which is between 1 and 200 µm.

Preferably, the mean diameter is between 5 and 100 µm, even more preferably between 20 and 50 µm.

The subject of the invention is therefore coagglomerates of mannitol, the laser mean volume diameter D4,3 of which is between 1 and 200 µm, and of granular starch.

The subject of the invention is also coagglomerates of mannitol, the laser mean volume diameter D4,3 of which is between 1 and 200 µm, and of granular starch, characterized in that they allow the preparation, by direct compression, of orodispersible tablets having notable properties both in terms of hardness and in terms of ability to disintegrate rapidly in the mouth.

For the purpose of the invention, the term "orodispersible tablets" is intended to mean tablets which, when placed in the mouth, disintegrate completely in less than 1 minute 30 seconds.

The subject of the invention is thus the use of the coagglomerates of mannitol, the laser mean volume diameter D4,3 of which is between 1 and 200 µm, and of granular starch, both as a binder and as a disintegrating agent for the preparation of orodispersible tablets.

Finally, the subject of the invention is orodispersible tablets, characterized in that the binding and disintegrating agent is made up of coagglomerates of mannitol, the laser mean volume diameter D4,3 of which is between 1 and 200 µm, and of granular starch.

The subject of the invention is more particularly coagglomerates of mannitol, the laser mean volume diameter D4,3 of which is between 1 and 200 µm, and of granular starch, characterized in that they have a disintegration behavior determined according to a test A such that the relaxation time measured is between 30 and 100 seconds and the swelling force is between 0.8 and 3 N.

This test A consists in producing, from the coagglomerates in accordance with the invention, tablets having a diameter of 16 mm and a thickness of 4 mm.

For this test A, 98% of coagglomerates according to the invention and 2% of magnesium stearate are mixed for five minutes using a Turbula T2C epicycloidal mixer (Willy A. Bachofen AG Maschinenfabrik, CH-4005 Basle).

The mixture is tabletted on a Fette Exacta 21 instrumented alternating press (Fette GmbH, D621493 Schwarzenbek), equipped with flat punches 16 mm in diameter.

The press is set so as to produce tablets of 1 g (i.e. 1000 mg±20 mg) and having a hardness of between 100 N and 110 N.

The tablet is then placed in a hollow receptacle with an internal diameter of 24 mm.

An initial force of 3 N is applied to the tablet by means of the cylindrical punch, 5 mm in diameter, of an Instron 4502 universal tensile-compression testing machine (USA, Canton-MA).

2 ml of spring water at the temperature of 20° C. are introduced at the bottom of the receptacle supporting the tablet, in contact with said tablet, using a precision pipette.

The change in the force applied is monitored for 200 seconds. The two parameters most particularly determined are the following:
- the relaxation time (expressed in seconds) disintegration of the tablet, corresponds to the time required for the initial force of 3 N to drop by half,
- the swelling (expressed in N), characterized by the immediate increase in the initial force linked to a gain in volume by the tablet at the time the water is introduced, is calculated as the maximum force achieved minus the force initially applied.

The values represent the mean calculated over three tests carried out for each of the coagglomerates in accordance with the invention that are tested.

The coagglomerates in accordance with the invention have, according to this test A, a disintegration behavior such that the relaxation time measured is between 30 and 100 seconds and the swelling force is between 0.8 and 3 N.

The coagglomerates according to the invention are also characterized by a viscosity, measured according to a test B, having a value of between 2.0 and 10.0 mPa·s when placed in suspension in water at a concentration of 42.8% by weight.

The test B consists in monitoring, at a temperature of 20° C., the change in viscosity of suspensions in water of coagglomerates of mannitol and of starch in accordance with the invention, for a period of 15 minutes, by means of the Physica MCR301 rheometer (Anton Paar).

The suspensions are prepared at a concentration of 42.8% (15 g of coagglomerates of mannitol and of starch in 20 g of demineralized water).

The coagglomerates in accordance with the invention have, according to this test B, a viscosity having a value of between 2.0 and 10.0 mPa·s when placed in suspension in water at a concentration of 42.8% by weight.

The coagglomerates according to the invention are characterized by their compression behavior, determined according to a test C.

The test C consists in measuring the compression force required to produce tablets with a hardness of between N and 110 N.

For this test C, 98% of coagglomerates according to the invention and 2% of magnesium stearate are mixed for five minutes using a Turbula T2C epicycloidal mixer (Willy A. Bachofen AG Maschinenfabrik, CH-4005 Basle).

The mixture thus obtained is tabletted on a Fette Exacta 21 instrumented alternating press (Fette GmbH, D621493 Schwarzenbek), equipped with flat punches 16 mm in diameter.

The press is set so as to produce tablets of 1 g (i.e. 1000 mg±20 mg) with a hardness of between 100 N and 110 N.

The hardness of the tablets is measured on an Erweka TBH30 GMD durometer (Erweka GmbH D63150 Heusenstamm).

The coagglomerates in accordance with the invention have, according to this test C, a compression behavior such that the compression force required to obtain said tablets with a hardness of between 100 N and 110 N is less than 40 kN.

The coagglomerates according to the invention are also characterized in that the mannitol/starch ratio is between 90/10 and 50/50.

Above 90% of mannitol or below 50% of mannitol, relative to the starch contained in the coagglomerates, the applicant company has observed that said coagglomerates do not have satisfactory disintegrating properties.

Preferably, a mannitol to starch ratio of between 80/20 and 65/35 will be chosen.

The coagglomerates of mannitol, the laser mean volume diameter D4,3 of which is between 1 and 200 μm, and of granular starch according to the invention are characterized in that the mannitol is in beta-crystalline form.

Mannitol is sold in three crystalline forms: alpha, beta and delta.

The applicant company has in fact found that the coagglomerates of mannitol, the laser mean volume diameter D4,3 of which is between 1 and 200 μm, and of granular starch, when the mannitol is present in an alpha or delta crystalline form, disintegrate about four times more slowly in the mouth than those containing a mannitol in beta-crystalline form.

The applicant company has found that mannitol in alpha- or delta-crystalline form, brought into contact with a small amount of water, as is the case in the oral cavity, dissolves and then recrystallizes in beta form.

However, this recrystallization is detrimental to the desired disintegration capacity.

The coagglomerates according to the invention have a laser mean volume diameter D4,3 of between 60 and 500 μm, preferably between 100 and 250 μm.

The particle size distribution values are determined on an LS 13-320 laser diffraction particle size analyzer from the company Beckman-Coulter, fitted with its (dry process) powder dispersion module, by following the operating guide and the specifications of the manufacturer.

The operating conditions of hopper screw speed and of vibration intensity of the dispersion chute are determined such that the optical concentration is between 4% and 12%, ideally 8%.

The measurement range of the LS 13-320 laser diffraction particle size analyzer is from 0.04 μm to 2000 μm. The results are calculated as % by volume, and expressed in μm.

The particle size distribution curve also makes it possible to determine the value of the mean volume diameter (arithmetic average) D4,3.

The coagglomerates according to the invention make it possible to prepare tablets which disintegrate in the mouth, according to a test D, in less than 60 seconds, preferably in less than 40 seconds.

The test D consists in carrying out an in vivo disintegration test with a panel of trained individuals. The panel is made up of five individuals. Each individual drinks a glass of water of at least 125 ml and then waits 30 seconds before placing a tablet on the tongue.

Throughout the disintegration period, the mouth should remain closed and the tongue should make only small movements.

The disintegration time corresponds to the period of time between the moment the tablet is placed in the mouth and the moment the tablet no longer has any cohesion, i.e. there remains at best only a suspension of granules or of powder in the mouth.

The five individuals of the panel test each tablet three times. The value retained for this test is the average of these fifteen disintegration times thus measured.

According to another embodiment of the invention, the coagglomerates comprise mannitol and starch and can, in addition, contain any suitable additive provided that it is not detrimental to the desired properties of the final granules, such as, in particular, flavorings, dyes, stabilizers, binders, lubricants or preservatives.

This may also involve pharmaceutical or plant-protection active ingredients, or detergents.

The Coagglomerates in Accordance with the Invention

The coagglomerates in accordance with the invention having the characteristics mentioned above can be obtained most particularly according to a method which comprises a step of spray-drying a suspension of mannitol crystals and of starch.

This objective had not been achieved up until then by means of the methods known to those skilled in the art and applicable both to mannitol and to starch. This is because the latter has the drawback, when thermal methods are used in an aqueous medium, of cooking and of thus losing its granular and therefore disintegrating nature.

Preferably, the following steps can be carried out:

a) preparing, at a temperature of between 15 and 25° C., a suspension of mannitol crystals and of granular starch, in which:
- the mannitol crystals have a laser mean volume diameter D4,3 of between 1 and 200 µm, preferably between 5 and 100 µm, even more preferably between 20 and 50 µm,
- the mannitol/starch ratio is between 90/10 and 50/50, and preferably between 80/20 and 65/35,
- the dry matter is between 40% and 60% by dry weight, b) maintaining said suspension of mannitol crystals and starch at the temperature between 15 and 25° C., c) spray-drying said suspension in an MSD-type spray-drierfitted with a high-pressure spray-drying nozzle with recycling of the fine particles at the top of the spray-drier, d) recovering the coagglomerates of mannitol and of starch thus obtained.

The first step therefore consists in preparing, at a temperature of between 15 and 25° C., a suspension of mannitol crystals and of starch, in which:
- the mannitol crystals have a laser mean volume diameter D4,3 of between 1 and 200 µm, preferably between 5 and 100 µm, even more preferably between 20 and 50 µm,
- the mannitol/starch ratio is between 90/10 and 50/50, and preferably between 80/20 and 65/35,
- the dry matter is between 40% and 60% by dry weight.

In the method in accordance with the invention, it is particularly advantageous to have a high content of mannitol crystals in the suspension of mannitol and of starch.

The use of a crystalline mannitol of fine particle size, i.e. having a laser mean volume diameter D4,3 of between 1 and 200 µm, preferably between 5 and 100 µm, even more preferably between 20 and 50 µm, is chosen because the applicant company has found that orthorhombic mannitol crystals greater than 200 µm in size reduce the homogeneity of the coagglomerates and, consequently, the cohesion of the tablets.

Moreover, a crystalline mannitol with a particle size of less than 1 µm cannot be used efficiently for the preparation of the mannitol and granular starch coagglomerates in accordance with the invention.

Since mannitol is not very soluble in water (maximum concentration of 18 g/l at 20° C.), it is thus chosen to prepare, at a temperature of between 15 and 25° C. (for example 20° C.), a suspension of mannitol and of starch having a dry matter of between 40% and 60% (for example 50%).

The starch content is also an important parameter, as is its ratio with respect to the mannitol.

A mannitol/starch ratio of between 90/10 and 50/50, and preferably between 80/20 and 65/35, is thus chosen.

The second step consists in maintaining said suspension of mannitol crystals and of starch at the temperature between 15 and 25° C.

The maintaining at this temperature makes it possible to stabilize the content of mannitol crystals in the suspension.

As will be exemplified hereinafter, excellent results are obtained when approximately 65% of the mannitol is in the form of crystals.

The third step thus consists in spray-drying said suspension in an MSD (i.e. Multi-Stage Dryer) type spray-drier fitted with a high-pressure spray-drying nozzle with recycling of the fine particles at the top of the spray-drier.

As will be exemplified hereinafter, the applicant company recommends using a MSD 20 type spray-drier sold by the company Niro.

The injection nozzle is chosen so as to obtain a pressure of between 20 and 50 bar, preferably of about 30 bar, for a flow rate of between 100 and 150 l/h, preferably about 120 l/h.

The inlet air temperatures are set in the following way:
- for the inlet air upstream of the top of the tower: temperature between 150 and 180° C., preferably 155° C.,
- for the static fluidized bed: temperature between 50 and 120° C., preferably 84° C.,
- for the vibrated fluidized bed: temperature of about 20° C.

The outlet temperature is thus between 55 and 80° C., preferably about 60° C.

Finally, the coagglomerates according to the invention are recovered at the spray-drier outlet.

The invention will be understood more clearly from the examples which follow, which are intended to illustrate the invention in a nonlimiting manner.

EXAMPLE 1: PREPARATION OF COAGGLOMERATES ACCORDING TO THE INVENTION

Various compositions of coagglomerates consisting of mannitol and of starch are prepared, by spray-drying according to the invention, at ratios of 90/10, 85/15, 80/20, 65/35 and 50/50, respectively.

Crystalline mannitol of fine particle size, sold by the applicant company under the name Mannitol 35, having a laser mean volume diameter of approximately 50 µm, and "extra-white" corn starch are used.

The operating conditions for producing these coagglomerates are represented in the following table 1.

TABLE 1

| Coagglomerates according to the invention | Mannitol/ starch ratio | Dry matter (%) | Pressure (bar) | Nozzle (spraying system type SK) | Tp upstream air (° C.) | Tp of the static fluidized bed (° C.) | Tp outlet air (° C.) |
|---|---|---|---|---|---|---|---|
| "A" | 90/10 | 50 | 20 | 52 * 21 | 170 | 84 | 75 |
| "B" | 85/15 | 52 | 25 | 52 * 21 | 175 | 84 | 70 |
| "C" | 80/20 | 55 | 30 | 52 * 21 | 155 | 84 | 60 |
| "D" | 65/35 | 55 | 25 | 52 * 21 | 160 | 84 | 60 |
| "E" | 50/50 | 57 | 25 | 52 * 21 | 160 | 84 | 65 |
| Control mannitol alone | 100/0 | 45 | 20 | 52 * 21 | 175 | 84 | 75 |

The characteristics of the coagglomerates of mannitol and of starch according to the invention are given in the following table 2.

TABLE 2

| Coagglomerates according to the invention | Laser particle size (D4,3- µm) | Viscosity at 42.8% of DM (mPa · s) | Relaxation time (s) | Swelling force (N) | Compression force (KN) | Hardness (N) | Disintegration in the mouth (s) |
|---|---|---|---|---|---|---|---|
| "A" | 230 | 3.6 | 80 | 2.08 | 29.3 | 110 | 43 |
| "B" | 150 | 3.8 | 81 | 0.96 | 32.1 | 100 | 48 |
| "C" | 123 | 3.8 | 59 | 2.17 | 30.4 | 110 | 36 |
| "D" | 124 | 2.7 | 51 | 2.77 | 35.6 | 102 | 35 |
| "E" | 198 | 2.6 | 42 | 2.73 | 39.6 | 100 | 39 |
| Control mannitol alone | 290 | 3.3 | 118 | 0.12 | 29.6 | 110 | 105 |

The behavior of the mannitol coagglomerates according to the invention is entirely satisfactory in terms of:
- disintegration behavior and disintegration time in the mouth, which reflect the ability of the granular starch to act as an effective disintegrating agent;
- viscosity at 42.8% of DM, which reflects the homogeneity of the coagglomerates resuspended, the added starch not modifying the behavior of said suspension;
- preserved compression force and hardness.

The best results are obtained for the coagglomerates of which the mannitol/starch ratio is preferably between 80/20 and 65/35.

EXAMPLE 2: PREPARATION OF COAGGLOMERATES ACCORDING TO THE INVENTION

Three coagglomerates consisting of mannitol and of starch at an 80/20 ratio are prepared, by spray-drying according to the invention, with Mannitol 35 crystalline mannitol and three different granular starches, "extra-white" corn starch, potato starch, and a hydroxypropyl-stabilized, phosphate-crosslinked waxy corn starch, sold by the applicant company under the name Clearam CR 20/10.

The operating conditions for producing these coagglomerates are represented in the following table 3.

TABLE 3

| Coagglomerates according to the invention | Starch incorporated | Dry matter (%) | Pressure (bar) | Nozzle (spraying system type SK) | Tp upstream air (° C.) | Tp of the static fluidized bed (° C.) | Tp outlet air (° C.) |
|---|---|---|---|---|---|---|---|
| "C" | Extra-white corn starch | 55 | 30 | 52 * 21 | 155 | 84 | 60 |
| "F" | Potato starch | 51 | 25 | 52 * 21 | 160 | 84 | 63 |
| "G" | Clearam CR 20 10 | 50 | 28 | 52 * 21 | 160 | 84 | 60 |

The characteristics of the coagglomerates of mannitol and of starch according to the invention are given in the following table 4.

TABLE 4

| Coagglomerates according to the invention | Laser particle size (D4,3-μm) | Viscosity at 42.8% of DM | Relaxation time (s) | Swelling force (N) | Compression force (KN) | Hardness (N) | Disintegration in the mouth (s) |
|---|---|---|---|---|---|---|---|
| "C" | 123 | 3.8 | 59 | 2.17 | 30.4 | 110 | 36 |
| "F" | 142 | 2.7 | 93 | 2.73 | 37.6 | 109 | 57 |
| "G" | 182 | 2.6 | 97 | 1.26 | 28.5 | 108 | 59 |

The behavior of the mannitol coagglomerates according to the invention is entirely satisfactory in terms of disintegration time in the mouth. The invention can be realized with native starches or modified starches which have retained a granular form.

EXAMPLE 3: PREPARATION OF COAGGLOMERATES ACCORDING TO THE INVENTION

Three coagglomerates consisting of mannitol and of starch at a ratio, respectively, of 80/20 are prepared by spray-drying, according to the invention, with "Extra-white" corn starch and three crystalline mannitol powders of different particle sizes, Mannitol 25 and Mannitol 35, sold by the applicant company and having, respectively, a laser mean volume diameter of approximately 25 μm and of approximately 50 μm, and a powder of crystalline mannitol having a laser mean volume diameter D4,3 of approximately 110 μm.

The operating conditions for producing these coagglomerates are represented in the following table 5.

TABLE 5

| Coagglomerates according to the invention | Mannitol powder | Dry matter (%) | Pressure (bar) | Nozzle (spraying system type SK) | Tp upstream air (° C.) | Tp of the static fluidized bed (° C.) | Tp outlet air (° C.) |
|---|---|---|---|---|---|---|---|
| "C" | Maltitol 35 | 55 | 30 | 52 * 21 | 155 | 84 | 60 |
| "H" | Maltitol 25 | 50 | 28 | 52 * 21 | 160 | 84 | 62 |
| "I" | Mannitol with a laser average diameter D4,3 of 110 μm | 52 | 30 | 52 * 21 | 155 | 84 | 60 |

The characteristics of the coagglomerates of mannitol and of starch according to the invention are given in the following table 6.

TABLE 6

| Coagglomerate according to the invention | Laser particle size (D4,3-μm) | Viscosity at 42.8% of DM | Relaxation time (s) | Swelling force (KN) | Compression force (N) | Hardness (N) | Disintegration in the mouth (s) |
|---|---|---|---|---|---|---|---|
| "C" | 123 | 3.8 | 59 | 2.17 | 30.4 | 110 | 36 |
| "H" | 99 | 3.9 | 53 | 2.40 | 30.7 | 105 | 30 |
| "I" | 150 | 2.4 | 61 | 1.39 | 32.5 | 104 | 38 |

The behavior of the mannitol coagglomerates according to the invention is entirely satisfactory in terms of disintegration time in the mouth.

EXAMPLE 4: COMPARATIVE EXAMPLE

The coagglomerates of mannitol and of starch "C" of example 1 are compared with compounds and mixtures as follows:
- coagglomerate of lactose and of starch prepared by the applicant company according to the teaching of its patent EP 1.175.899,
- mannitol sold by the applicant company under the trademark Pearlitol® 50C,
- physical mixture of Pearlitol® 50C and of "extra-white" corn starch in an 80/20 proportion,
- coagglomerate of starch and of mannitol in an 80/20 ratio, prepared by spray-drying a suspension containing 32% of dry matter and heated to 50° C. so as to completely solubilize the mannitol "F" present. This coagglomerate is in predominantly alpha-crystalline form.

The following table 7 gives the results obtained.

TABLE 7

| | Laser particle size (D4,3-μm) | Viscosity at 42.8% of DM | Relaxation time (s) | Swelling force (N) | Compression force (KN) | Hardness (N) | Disintegration in the mouth (s) |
|---|---|---|---|---|---|---|---|
| Lactose + starch coagglomerate (85/15) | 125 | 2.2 | 70 | 0.68 | 33.3 | 100 | 37 |
| Pearlitol® 50C | 50 | 4.2 | ND | ND | ND | ND | ND |
| Physical mixture Pearlitol® 50C + starch (80/20) | Approximately 45 | 3 | ND | ND | ND | ND | ND |
| "F" | 120 | 208 | 180 | 0.54 | 25.2 | 108 | 122 |
| "C" | 123 | 3.8 | 59 | 2.17 | 30.4 | 111 | 36 |

It proved to be impossible to prepare tablets with Pearlitol® 50C alone or as a mixture with the starch. The Pearlitol® 50C and the "extra-white" corn starch have a very fine particle size and, as a result, do not exhibit a free flow. It is therefore impossible for them to fill the die, which is the first step in obtaining a tablet on a tableting press.

EXAMPLE 5: DEVELOPMENT BY DIRECT COMPRESSION AND CHARACTERIZATION OF ORODISPERSIBLE TABLETS WITH ACTIVE INGREDIENTS a) Formulation of the Orodispersible Tablets by Direct Compression The coagglomerate of mannitol of fine particle size and of native starch is used as binder, as diluting agent and as disintegrating agent. Plant magnesium stearate (Barlôcher) is used as lubricant. The composition of each tablet is described in the following table 8.

TABLE 8 formulation of the orodispersible tablets with active ingredients

| | Formulation 1 | Formulation 2 | Formulation 3 |
|---|---|---|---|
| Mannitol/native starch coagglomerate | 94.6% | 74.6% | 97.4% |
| Hydrochlorothiazide | 5.0% | | |
| Roche crystalline ascorbic acid | | 25.0% | |
| Sodium fluoride | | | 2.2% |
| Plant magnesium stearate | 0.4% | 0.4% | 0.4% |
| Total | 100% | 100% | 100% |

The coagglomerate and the active molecule are mixed for five minutes using a Turbula T2C epicycloidal mixer (Willy A. Bachofen AG Maschinenfabrik, CH-4005 Basle). The lubricant is added to this mixture. The formulation is mixed for five minutes in the epicycloidal mixer.

The mixture is tableted on a Korsch XP1 instrumented alternative press (Korsch AG, Breitenbachstraße 1, Germany), fitted with flat punches having a diameter suitable for the formulation (table 9) with beveled edges, at a rate of 20 tablets per minute.

TABLE 9 tableting on the Korsch XP1 alternative press.

| | Formulation 1 | Formulation 2 | Formulation 3 |
|---|---|---|---|
| Punch diameter (mm) | 13 | 16 | 7 | b) Characterization of the Orodispersible Tablets

The tablets formulated are evaluated according to the pharmacopeia methods: weight (Erweka TBH 30N precision balance), thickness (micrometer), hardness (Schleuniger), friability (Erweka). The disintegration time in the mouth is determined by carrying out the test E as described in this patent. The results are summarized in the following table 10.

TABLE 10

|  | Formulation 1 | Formulation 2 | Formulation 3 |
|---|---|---|---|
| Weight (mg ± standard deviation) | 505.4 ± 0.67 | 1020 ± 3.41 | 104.4 ± 0.19 |
| Thickness (mm ± standard deviation) | 2.96 ± 0.007 | 3.74 ± 0.011 | 1.93 ± 0.01 |
| Hardness (N ± standard deviation) | 77.4 ± 1.35 | 68.8 ± 6.99 | 82.8 ± 2.28 |
| Friability (%) | 0.26 | 2.25 | 0.16 |
| Disintegration time in the mouth (s ± standard deviation) | 20 ± 5 | 28 ± 4 | 22 ± 2 |

The formulations developed contain only three ingredients: the mannitol/starch coagglomerate, the active agent, and the compression lubricant. The coagglomerate according to the invention therefore makes it possible to rapidly and easily formulate orodispersible tablets, although the formulation of the latter is reputed to be complex. Furthermore, all three of these tablets with active ingredients have a very short disintegration time in the mouth, less than 30 seconds, as recommended by the health authorities.

The invention claimed is:

1. Orodispersible tablet comprising:
coagglomerates of beta-crystalline structured mannitol and granular starch in a mannitol/starch ratio of between 90/10 and 50/50, the mannitol having a laser mean volume diameter D4,3 of between 1 and 50 µm, the coagglomerates having a laser mean volume diameter D4,3 of between 100 and 250 µm and a viscosity value, when measured according to a test B, of between 2.0 and 10.0 mPa·s, when placed in suspension in water at a concentration of 42.8% by weight,
at least one compression lubricant comprising magnesium stearate, and
at least one active agent,
wherein said tablet has a disintegration rate of less than 60 seconds and is free of supplemental disintegrants.

2. The tablet as claimed in claim 1, wherein the coagglomerates have a viscosity value of between 2.0 and about 3.6 mPa·s.

3. The tablet as claimed in claim 1, wherein the mannitol/starch ratio is between 80/20 and 65/35.

4. The tablet as claimed in claim 1, wherein the starch is chosen from the group consisting of standard corn starch, "extra-white" corn starch and potato starch, taken alone or in combination.

5. The tablet as claimed in claim 1, wherein the coagglomerates disintegrate in the mouth, according to a test D, in less than 50 seconds.

6. The tablet of claim 5, wherein the coagglomerates disintegrate in the mouth, according to a test D in less than 40 seconds.

7. Orodispersible tablet comprising:
binders and disintegrating agents consisting of coagglomerates of mannitol in beta-crystalline form and granular starch in a mannitol/starch ratio between 90/10 and 50/50, the mannitol having a laser mean volume diameter D4,3 between 1 and 200 µm, the coagglomerates having a laser mean volume diameter D4,3, between 60 and 500 µm and a disintegration behavior such that the relaxation time measured according to this test A, is between 30 and 100 seconds,
wherein said tablet has a disintegration rate of less than 60 seconds and is free of supplemental disintegrants.

8. Orodispersible tablet comprising:
coagglomerates of beta-crystalline structured mannitol and granular starch in a mannitol/starch ratio of between 90/10 and 50/50, the mannitol having a laser mean volume diameter D4,3 between 1 and 200 µm and the coagglomerates having a laser mean volume diameter D4,3, of between 60 and 500 µm;
at least one compression lubricant;
at least one active agent; and
a disintegration rate of less than 60 second,
wherein said tablet is free of supplemental disintegrants.

9. The tablet according to claim 7, wherein the mannitol/starch ratio is between 80/20 and 65/35.

10. The tablet according to claim 7, wherein the mannitol/starch ratio is between 80/20 and 65/35 and relaxation time of said coagglomerate, when measured according to this test A, is between 30 and 100 seconds.

11. The tablet according to claim 8, wherein the mannitol/starch ratio is between 80/20 and 65/35 and relaxation time of said coagglomerate, when measured according to this test A, is between 30 and 100 seconds.

12. The tablet according to claim 8, wherein the mannitol/starch ratio is between 80/20 and 65/35.

13. The tablet according to claim 8, wherein the mannitol/starch ratio is between 80/20 and 65/35 and relaxation time of said coagglomerate, when measured according to this test A, is between 30 and 100 seconds.

14. The tablet according to claim 7, wherein the mannitol/starch ratio is between 80/20 and 65/35 and relaxation time of said coagglomerate, when measured according to this test A, is between 30 and 100 seconds.

15. Orodispersible tablet comprising:
at least one compression lubricant;
at least one active agent; and
coagglomerates of beta-crystalline structured mannitol and granular starch in a mannitol/starch ratio of between 90/10 and 50/50, the coagglomerates have a viscosity value of between 2.0 and 10.0 mPa·s when placed in suspension in water at a concentration of 42.8% by weight,
wherein the tablet has a disintegration rate of less than 60 second and is free of supplemental disintegrants.

* * * * *